United States Patent
Koizumi

(10) Patent No.: US 11,951,256 B2
(45) Date of Patent: Apr. 9, 2024

(54) OXYGEN THERAPY SYSTEM

(71) Applicant: Teijin Pharma Limited, Tokyo (JP)

(72) Inventor: Ryo Koizumi, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1231 days.

(21) Appl. No.: 16/498,152

(22) PCT Filed: Mar. 19, 2018

(86) PCT No.: PCT/JP2018/010820
§ 371 (c)(1),
(2) Date: Sep. 26, 2019

(87) PCT Pub. No.: WO2018/180708
PCT Pub. Date: Oct. 4, 2018

(65) Prior Publication Data
US 2021/0100967 A1    Apr. 8, 2021

(30) Foreign Application Priority Data

Mar. 31, 2017   (JP) .............................. 2017-070668

(51) Int. Cl.
*A61M 16/00*   (2006.01)
*A61B 5/1455*   (2006.01)
(Continued)

(52) U.S. Cl.
CPC ........ *A61M 16/024* (2017.08); *A61M 16/101* (2014.02); *G16H 10/60* (2018.01);
(Continued)

(58) Field of Classification Search
CPC ...... A61M 2230/202; A61M 2230/205; A61M 16/101; A61M 16/1005; A61M 16/022;
(Continued)

(56) References Cited

U.S. PATENT DOCUMENTS 4,773,422 A * 9/1988 Isaacson ............ A61B 5/14551
                                                                600/326
6,142,149 A * 11/2000 Steen .................... A61M 16/00
                                                                128/204.23
(Continued)

FOREIGN PATENT DOCUMENTS

| CN | 104399164 A | 3/2015 |
| CN | 104841048 A | 8/2015 |

(Continued)

OTHER PUBLICATIONS

Machine Translation of JP5986413B2_Description_Feb. 9, 2023 (Year: 2016).*

(Continued)

*Primary Examiner* — Kendra D Carter
*Assistant Examiner* — Mautin I Ashimiu
(74) *Attorney, Agent, or Firm* — Sughrue Mion, PLLC

(57) ABSTRACT

An oxygen therapy system receives data for an elapsed time such as a flow rate of oxygen gas, and a blood oxygen level or a carbon dioxide partial pressure in arterial blood (PaCO2) level of a user, from an oxygen supply device, calculates a proportion of a duration for each oxygen gas flow rate during which the blood oxygen level or PaCO2 is in a prescribed range from the acquired data in which the oxygen gas flow rate fluctuates with the blood oxygen level or carbon dioxide partial pressure in arterial blood (PaCO2), and displays the calculated data as a histogram or pie graph on a terminal which a healthcare worker such as a physician operates.

10 Claims, 3 Drawing Sheets

(51) Int. Cl.

| | | |
|---|---|---|
| *A61M 16/10* | (2006.01) | |
| *G16H 10/60* | (2018.01) | |
| *G16H 15/00* | (2018.01) | |
| *G16H 20/10* | (2018.01) | |
| *G16H 20/40* | (2018.01) | |
| *G16H 40/40* | (2018.01) | |
| *G16H 40/67* | (2018.01) | |
| *G16H 50/30* | (2018.01) | |
| *G16H 50/70* | (2018.01) | |

(52) U.S. Cl.
CPC ............ *G16H 15/00* (2018.01); *G16H 20/40* (2018.01); *G16H 40/40* (2018.01); *G16H 40/67* (2018.01); *G16H 50/30* (2018.01); *G16H 50/70* (2018.01); *A61M 2205/3334* (2013.01); *A61M 2205/502* (2013.01); *A61M 2230/202* (2013.01); *A61M 2230/205* (2013.01)

(58) Field of Classification Search
CPC .......... A61M 16/024; A61M 2016/102; A61M 2205/3334; A61M 2205/502; A61M 2230/502; A61B 5/7275; A61B 5/14542; A61B 5/14551; A61B 5/743; A61B 5/083; A61B 5/0833; A61B 5/0836; G16H 20/40; G16H 10/60; G16H 15/00; G16H 20/10
See application file for complete search history.

(56) References Cited

U.S. PATENT DOCUMENTS

| | | | |
|---|---|---|---|
| 9,364,623 B2 * | 6/2016 | Lellouche | ............. A61M 16/00 |
| 9,750,442 B2 * | 9/2017 | Olsen | ................. A61B 5/14542 |
| 2008/0156328 A1 | 7/2008 | Taube | |
| 2008/0183057 A1 | 7/2008 | Taube | |
| 2013/0150734 A1 | 6/2013 | Orr et al. | |
| 2014/0007870 A1 | 1/2014 | Fraanberg et al. | |

FOREIGN PATENT DOCUMENTS

| | | | | |
|---|---|---|---|---|
| JP | 2008-067941 A | | 3/2008 | |
| JP | 2013-208215 A | | 10/2013 | |
| JP | 2013208215 A | * | 10/2013 | ............ A61M 16/00 |
| JP | 2013-543389 A | | 12/2013 | |
| JP | 2014-064772 A | | 4/2014 | |
| JP | 5986413 B2 | * | 9/2016 | ............ A61M 16/00 |
| JP | 5986413 B2 | | 9/2016 | |

OTHER PUBLICATIONS

Communication, dated Feb. 27, 2020, issued by the European Patent Office in counterpart European Patent Application No. EP 18 77 6651.

International Search Report of PCT/JP2018/010820 dated Jun. 26, 2018 [PCT/ISA/210].

Communication, dated Jun. 3, 2021, issued by The State Intellectual Property Office of P.R. of China in Application No. 201880022141.X.

Communication, dated May 26, 2020, issued by the Japanese Patent Office in counterpart Japanese Patent Application No. 2019-509351.

* cited by examiner

[Fig. 1]
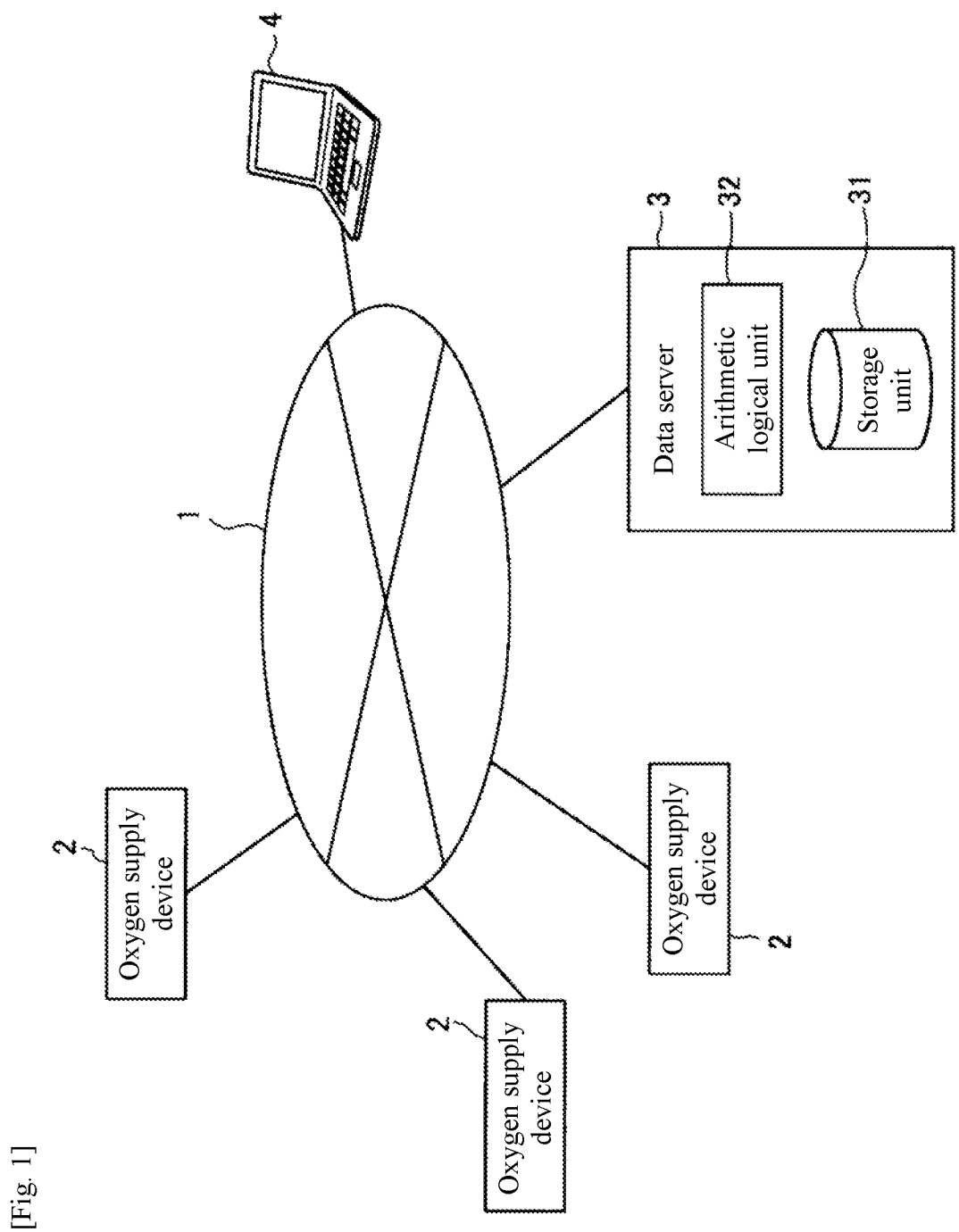

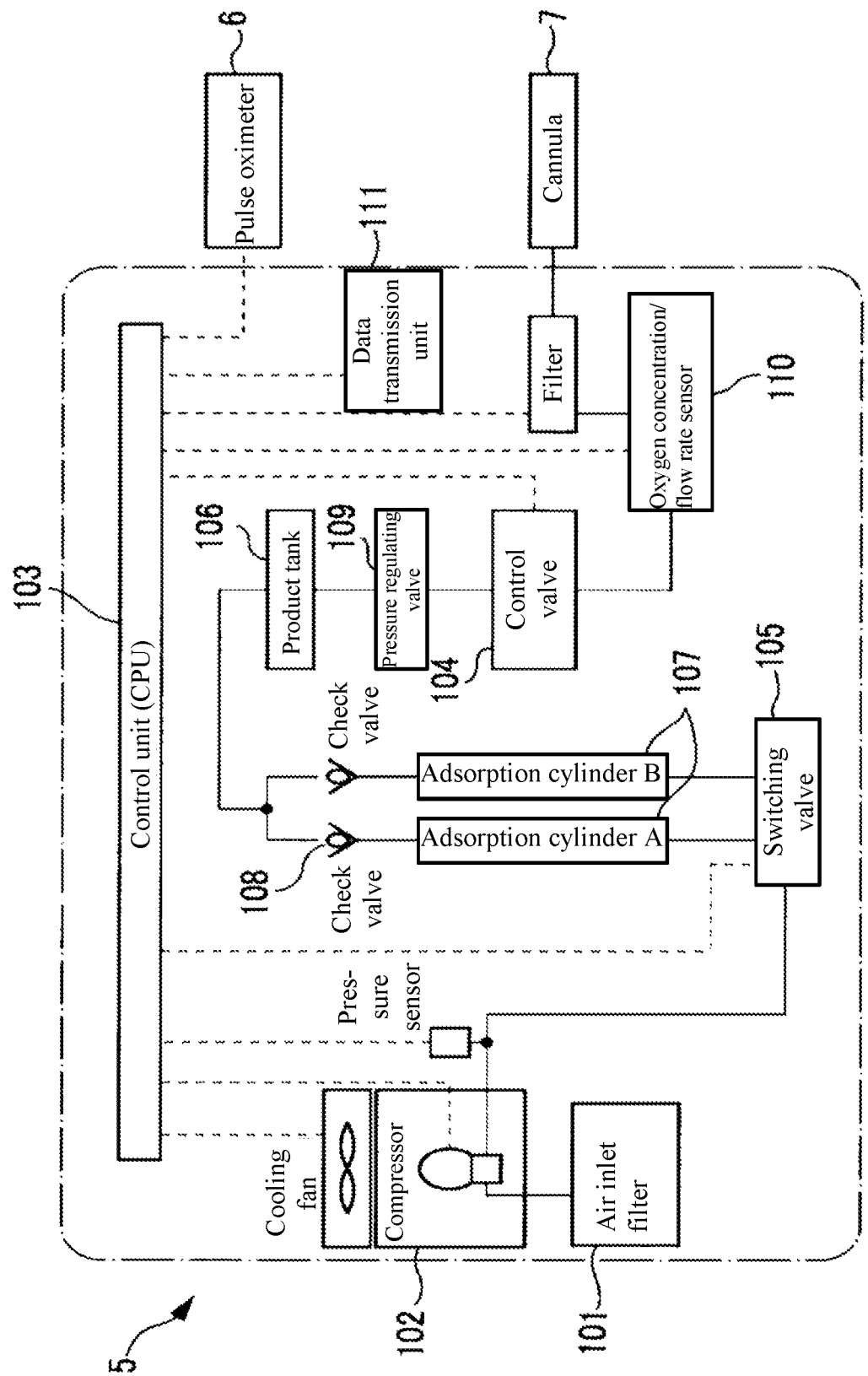
[Fig. 2]

[Fig. 3]
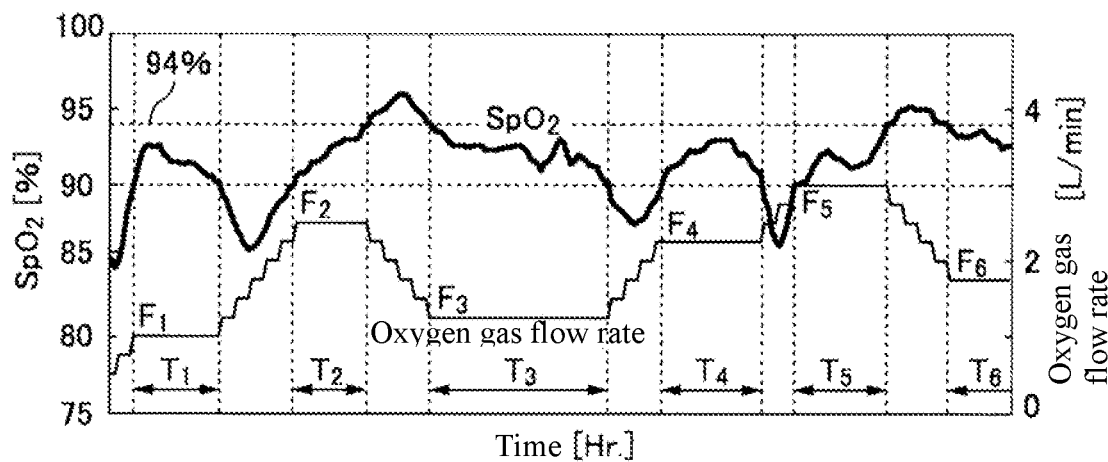
[Fig. 4]
| O₂ gas flow rate [LPM] | Proportion of duration within specified SpO2 range | SpO2 Ave. [%] | PaCO2 Ave. [mmHg] | HR Ave. [Times/min] | BPM Ave. [Times/min] |
|---|---|---|---|---|---|
| 0.25 | 3% | 85 | 35 | 90 | 30 |
| 0.75 | 7% | 88 | 37 | 85 | 28 |
| 1.00 | 20% | 90 | 38 | 80 | 25 |
| 1.25 | 50% | 92 | 40 | 75 | 23 |
| 1.75 | 10% | 94 | 42 | 70 | 20 |
| 2.00 | 5% | 96 | 44 | 65 | 18 |
| 3.00 | 5% | 96 | 45 | 65 | 18 |
| 4.00 | | | | | |
| 5.00 | | | | | |

OXYGEN THERAPY SYSTEM

CROSS REFERENCE TO RELATED APPLICATIONS

This application is a National Stage of International Application No. PCT/JP2018/010820, filed Mar. 19, 2018, claiming priority to Japanese Patent Application No. 2017-070668, filed Mar. 31, 2017.

TECHNICAL FIELD

The present invention relates to an oxygen therapy system that, in an oxygen therapy with inhalation of a high concentration oxygen gas using an oxygen supply device, provides data of patients to a healthcare worker such as a physician and the like (hereinafter referred to as "physician") who determines a prescription of the oxygen gas.

BACKGROUND ART

An oxygen therapy is regarded as a therapy for chronic respiratory disease such as chronic obstructive pulmonary disease, pulmonary tuberculosis sequelae and pulmonary fibrosis and the like. The oxygen therapy aims to improve/prevent hypoxemia by raising oxygen partial pressure in arterial blood (PaO2) of patients through administration of high concentration oxygen gas. A home oxygen therapy is a therapy in which a patient as a user of the oxygen supply device operates the device according to the prescription of a physician, and receives the oxygen therapy at home. In the home oxygen therapy, the oxygen gas for inhalation is supplied from the oxygen supply device such as oxygen concentration device and an oxygen cylinder described in PTL 1 or 2. Generally, an oxygen concentration device is used at home and a small and light-weight oxygen cylinder is often used outside home, such as going to hospital and shopping, for their convenience and ease of maintenance at use.

The patients receiving a home oxygen therapy receive the prescription such as flow rate and the like on the oxygen gas for inhalation from a physician at a medical institution. The physician measures a blood oxygen level, carbon dioxide partial pressure in arterial blood (PaCO2) and the like of the patient who comes for a medical examination, and gives a prescription, suitable for the patient concerning the disease and its severity, on a flow rate of the oxygen gas for inhalation based on the knowledge and experience of the physician. In PTL 2, proposed is a system that displays how the percutaneous carbon dioxide partial pressure (PtcCO2) fluctuates while supplying the prescribed oxygen gas.

CITATION LIST

Patent Literature

[PTL 1] Japanese Unexamined Patent Application Publication No. 2014-64772
[PTL 2] Japanese Patent No. 5986413

SUMMARY OF INVENTION

Technical Problem

For each patient, biological information such as blood oxygen level, carbon dioxide partial pressure in arterial blood (PaCO2) and the like usually varies according to an activity state such as being at rest, elaboration, sleep and the like as well as a disease condition of each patient. Thus, for a physician who is going to prescribe, for example, a suitable oxygen gas for a patient during sleep, it is desirable to examine the blood oxygen level, carbon dioxide partial pressure in arterial blood (PaCO2), and the like of the patient during sleep as well as during a medical examination. However, it is a great burden for the physician to examine the data over several hours or more during sleep and find some sort of guide line for the prescription.

The present invention is based on the above consideration, and aims to provide an oxygen therapy system that can acquire biological information such as the blood oxygen level, carbon dioxide partial pressure in arterial blood (PaCO2), and the like of the patient receiving home oxygen therapy, and present the information on the effect for each flow rate of the oxygen gas.

Solution to Problem

The present invention includes the following embodiments of (1)-(6).

(1) An oxygen therapy system of the present invention comprising:
a storage unit that receives, from an oxygen supply device which controls a flow rate of an oxygen gas for inhalation based on a blood oxygen level or a carbon dioxide partial pressure in arterial blood (PaCO2) of a user so that a blood oxygen level or a level of carbon dioxide partial pressure in arterial blood (PaCO2) is in a prescribed range, data for an elapsed time such as a flow rate value of the oxygen gas, and a blood oxygen level or a level of carbon dioxide partial pressure in arterial blood (PaCO2) of the user and stores the data, an arithmetic logical unit that calculates, from the data during a predetermined period, a proportion of a duration, for each flow rate of the oxygen gas, during which the blood oxygen level or the carbon dioxide partial pressure in arterial blood (PaCO2) of the user is in the prescribed range, and a display unit that displays the proportion of the duration calculated by the arithmetic logical unit.

(2) The oxygen therapy system according to (1), wherein the blood oxygen level is percutaneous arterial oxygen saturation (SpO2) measured using a pulse oximeter.

(3) The oxygen therapy system according to (1) or (2), wherein the oxygen supply device is an oxygen concentration device.

(4) The oxygen therapy system according to (1) or (2), wherein the oxygen supply device supplies a high-pressure oxygen gas filled in cylinder as the oxygen gas.

(5) The oxygen therapy system according to any one of (1) to (4), wherein the proportion of the duration is displayed as a histogram or a pie graph on the display unit.

(6) The oxygen therapy system according to any one of (1) to (5), wherein the proportion of the duration to the predetermined period is displayed as a histogram or a pie graph on the display unit for at least one selected from the flow rate value of the oxygen gas, the blood oxygen level of the user, and the level of carbon dioxide partial pressure in arterial blood (PaCO2).

Advantageous Effects of Invention

In accordance to the present invention, provided is an oxygen therapy system that acquires biological information such as blood oxygen level, carbon dioxide partial pressure in arterial blood (PaCO2), and the like of the patient receiving home oxygen therapy, and presents the information on the effect for each flow rate of the oxygen gas.

BRIEF DESCRIPTION OF DRAWINGS

FIG. 1 shows the configuration of the oxygen therapy system.
FIG. 2 shows the configuration of the oxygen concentration device that is an oxygen supply device.
FIG. 3 schematically shows a waveform of SpO2 and a flow rate of the oxygen gas.
FIG. 4 shows an example of data displayed on a terminal.

DESCRIPTION OF EMBODIMENTS

Embodiments of the present invention is explained with reference to Figs as follows.

FIG. 1 shows the configuration of the oxygen therapy system that is an embodiment of the present invention. Oxygen supply device 2 has a feedback function to control a flow rate of the oxygen gas for inhalation supplied to a user who is also a patient so that the blood oxygen level or the level of carbon dioxide partial pressure in arterial blood (PaCO2) is in the prescribed range, based on the measured blood oxygen level or the carbon dioxide partial pressure in arterial blood (PaCO2) of the user.

In the oxygen therapy system, data server 3 receives, from oxygen supply device 2, data including the flow rate of the oxygen gas, the measured level of blood oxygen or carbon dioxide partial pressure in arterial blood (PaCO2) of the patient, and the range of level prescribed by a physician on blood oxygen or carbon dioxide partial pressure in arterial blood (PaCO2), and the like during the oxygen therapy under the feedback mode of oxygen supply device 2 and saves the data in storage unit 31.

When requested from terminal 4 operated by a physician, data server 3 reads the data from storage unit 31 and, in arithmetic logical unit 32, calculates a proportion of the duration, for each flow rate of the oxygen gas, during which the blood oxygen level or the carbon dioxide partial pressure in arterial blood (PaCO2) is in the prescribed range, and sends the calculated result to terminal 4. The display unit of terminal 4 displays the proportion of the duration for each flow rate of the oxygen gas as a graph. Oxygen supply device 2, data server 3, terminal 4 are connected to communication network 1, and can communicate with each other.

Communication network 1 is not limited in particular and can adopt those well-known such as Internet, a mobile communications network, a leased line network and the like. In addition, oxygen supply device 2 and terminal 4 connected to communication network 1 each may be plural.

The explanation is made as follows taking an example of the case where oxygen supply device 2 is oxygen concentration device 2 having an SpO2 feedback function to control a flow rate of the oxygen gas for inhalation based on percutaneous arterial oxygen saturation (SpO2) which corresponds to a blood oxygen level.

FIG. 2 illustrates the configuration of the oxygen concentration device 2 having an SpO2 feedback function. The oxygen concentration device 2 is a device that isolates nitrogen contained in the air and supplies a high concentration oxygen (oxygen enriched gas) as an oxygen gas for inhalation. The solid lines and the dotted lines connecting each component shown in FIG. 2 represent main gas flow paths and main paths of electric signal such as control signal, respectively.

The raw material air is taken into main body 5 of the oxygen concentration device through the air inlet provided with air inlet filter 101 that removes foreign substances such as dusts. At this time, about 21% of oxygen gas, about 77% of nitrogen gas, 0.8% of argon gas, and 1.2% of carbon dioxide and other gases are contained in the air. The oxygen concentration device 2 concentrates the oxygen gas necessary for respiration gas and takes it out.

The raw material air taken into main body 5 of the oxygen concentration device is compressed by compressor 102, transferred to adsorption cylinder 107 filled with adsorbent made of zeolite and the like which selectively adsorbs nitrogen molecules. Control unit 103, by operating switching valve 105, switches a target adsorption cylinder in turn and supplies the raw material air to the cylinder, and the nitrogen gas that occupies about 77% of the raw material air is selectively adsorbed and removed in the adsorption cylinder 107.

The nitrogen gas in the air is adsorbed on the adsorbent in adsorption cylinder 107 at the compressed state, and the oxygen concentrated gas mainly composed of the unadsorbed oxygen is taken out of adsorption cylinder 107. The oxygen concentrated gas taken out flows into product tank 106 through check valve 108 provided to prevent backflow into adsorption cylinder 107 and is accumulated in product tank 106. The oxygen concentrated gas accumulated in product tank 106 is an oxygen gas with high concentration of, for example, 95%.

Control unit 103 controls control valve 104 to adjust the oxygen gas to a flow rate prescribed by a physician and supplies the oxygen gas to a patient through cannula 7. Oxygen concentration/flow rate sensor 110 feedbacks values of flow rate and oxygen concentration of the supplied oxygen gas to control unit 103, and manufacture and supply of the oxygen gas by the oxygen concentration device 2 are controlled.

When oxygen concentration device is set to an SpO2 feedback mode, control unit 103 checks whether the SpO2 measured by pulse oximeter 6 is in the range (e.g., 90% or more, 94% or less) prescribed by a physician. Then, control unit 103 controls control valve 104 and increases/decreases a flow rate of the oxygen gas supplied through cannula 7 so that the measured SpO2 is in the prescribed range. Control part 103 increases/decreases the flow rate of the oxygen gas when the measured level of SpO2 is below/over the prescribed range of SpO2. Thus, in the SpO2 feedback mode, the oxygen gas flow rate is not kept at a constant value, but is controlled so that the measured SpO2 is in the prescribed range, and thus changes over time.

FIG. 3 illustrates schematically the change of the oxygen gas flow rate over time accompanying the fluctuation of the SpO2 of a user in sleep when the SpO2 feedback mode is set. When the prescribed range of SpO2 is 90% or more and 94% or less, control unit 103 increases the oxygen gas flow rate if the SpO2 becomes smaller than 90% and decreases the oxygen gas flow rate if the SpO2 becomes larger than 94%. Thus, in the SpO2 feedback mode, the data is obtained that shows a change of the oxygen gas flow rate over time in response to the fluctuation of SpO2 as in FIG. 3.

The oxygen inhalation therapy system can be provided with a function to display the temporal change data of SpO2 and oxygen gas flow rate on terminal 4 as a graph as in FIG. 3. A display method of the temporal change of SpO2 and oxygen gas flow rate is not limited to the graph form of FIG.

3. A histogram or pie graph may be adopted as a graph for displaying the proportion of the duration for each rank of the SpO2 or the oxygen gas flow rate calculated from the temporal change data during the predetermined period. The display of the temporal change data of SpO2 and oxygen gas flow rate on terminal 4 enables confirmation of how the SpO2 is controlled and how the oxygen gas flow rate changes over time.

Data transmission unit 111 of oxygen concentration device 2 sends data of the oxygen gas flow rate and the SpO2 changing over time to data server 3 through communication network 1. The data of the oxygen gas flow rate and the SpO2 transmitted by oxygen concentration device 2 are received by data server 3, and stored in storage unit 31. A physician to prescribe an oxygen gas flow rate for a patient sends information such as "ID" for identifying the patient, "T" for time range for processing the data, and the like from terminal 4 to data server 3, and requests transmission of the data.

When receiving the request from terminal 4, data server 3 reads from storage unit 31 the information on the patient specified by "ID" such as data of oxygen gas flow rate and SpO2, specified range of SpO2, and the like, and arithmetic logical unit 32 calculates the total of the duration (Ttotal), during which the SpO2 was in the specified range, over the specified time range (T). Here, the specified range of SpO2 is, for example, the SpO2 range prescribed beforehand by a physician for an SpO2 feedback control by oxygen concentration device 2.

In FIG. 3, Tn (FIG. 3 exemplifies n of 1-6.) is a duration during which the measured SpO2 is in the prescribed range of 90% or more and 94% or less, and Fn (FIG. 3 exemplifies n of 1-6.) is the oxygen gas flow rate in the same duration. Arithmetic logical unit 32 divides the total duration (Ttotal) into durations, T1, T2, T3 . . . Tn for each flow rate value of the oxygen gas, F1, F2, F3 . . . Fn as shown in FIG. 3, and displays Tn/Ttotal as a histogram of the proportion of the duration of each flow rate value of the oxygen gas Fn to the duration during which the SpO2 was in the specified range on the display unit of terminal 4. Note that, the display may be in the graph form of a pie graph as well as a histogram.

FIG. 4 is an example of the display screen displayed on terminal 4. The histogram illustrates the distribution of the duration corresponding to each flow rate value of the oxygen gas (Fn) in the total duration (Ttotal) during which the SpO2 is in the specified range of 90% or more and 94% or less, and it is easily understood from the display screen of FIG. 4 that the duration for an oxygen gas flow rate of, for example, 1.25 L/min accounts for 50% of the total duration (Ttotal). In addition to the histogram, arithmetic logical unit 32 of the data server can calculate an average value of SpO2 for each flow rate of the oxygen gas and make terminal 4 display also the calculated result. Further, in the oxygen therapy system, measured values of carbon dioxide partial pressure in arterial blood (PaCO2), heart rate (HR), respiratory frequency (BMP) and the like as well as SpO2 may be received by data server 3 and stored in storage unit 31, average values of the measured data are calculated for each flow rate of the oxygen gas in arithmetic logical unit 32 and the results may be added to the histogram and displayed.

A physician who intends to prescribe, for example, an oxygen gas flow rate for a patient during sleep uses the oxygen therapy system with a prescribed SpO2 range under the SpO2 feedback mode and measures temporal change data of SpO2 and oxygen gas flow rate of the patient overnight. The measurement may be carried out in the medical institution or at the home of the patient. The physician confirms the measured data using a graph as in FIG. 3 and a histogram for each of SpO2 and oxygen gas flow rate, and the like, and checks how the SpO2 is controlled and how the oxygen gas flow rate changes over time.

Specifically, by specifying the period of the patient's sleep as the time range (T) using terminal 4, the physician makes terminal 4 display a graph for each oxygen gas flow rate as in FIG. 4 from data server 3 on the display unit. The oxygen therapy system displays a graph that represents the distribution of the proportion of the duration corresponding to each flow rate value of the oxygen gas (Fn) in the total duration (Ttotal) during which the SpO2 is in the prescribed range, and the like, and thus assists judgement by the physician prescribing the flow rate of the oxygen gas and the like for the patient in sleep.

Although the oxygen therapy system of the embodiment is explained taking an example of oxygen concentration device 2, the oxygen supply equipment 2 may be an oxygen cylinder with an SpO2 feedback function. Also, in addition to the SpO2 feedback function, oxygen supply device 2 may adopt a feedback function for carbon dioxide partial pressure in blood (PaCO2).

An SpO2+PaCO2 feedback function that feedbacks measured levels of SpO2 and PaCO2 checks whether the measured SpO2 and PaCO2 are within a range prescribed by a physician for SpO2 and PaCO2. Then, control valve 104 is controlled, when the measured SpO2 level is lower than the prescribed range and the measured PaCO2 level is lower than the prescribed range, so as to increase the flow rate of the oxygen gas supplied from cannula 7, and when the measured PaCO2 level is higher than the prescribed range, so as to decrease the flow rate of the oxygen gas. Thus, in the SpO2+PaCO2 feedback mode, data is also obtained that shows a fluctuation of the oxygen gas flow rate in response to the SpO2+PaCO2. The oxygen therapy system displays a histogram of the distribution of the duration corresponding to each flow rate value of the oxygen gas in the total duration during which SpO2 and PaCO2 both are in the prescribed range, and the like on the display unit of terminal 4, and thus assists judgement of the physician.

Though a preferred embodiment of the present invention was explained in detail as above, the present invention is not limited to an embodiment mentioned above, and various kinds of variation and modification are possible within the contents of the present invention described in the scope of claims.

INDUSTRIAL APPLICABILITY

In accordance with the present invention, display of the effect by each flow rate of the oxygen gas using data of changing oxygen gas flow rates over time enables an efficient prescription of the oxygen gas flow rate for a patient receiving home oxygen therapy.

REFERENCE SIGNS LIST

1. Communication network
2. Oxygen supply device, oxygen concentration device
3. Data server
31. Storage unit
32. Arithmetic logical unit
4. Terminal
5. Oxygen concentration device main body
6. Pulse oximeter
7. Cannula
101. Air inlet filter 102. Compressor
103. Control unit
104. Control valve
105. Switching valve
106. Product tank
107. Adsorption cylinder
108. Check valve
109. Pressure regulating valve
110. Oxygen concentration/flow rate sensor
111. Data transmission unit

The invention claimed is:

1. An oxygen inhalation therapy system comprising:
a storage unit that receives and stores, from an oxygen supply device which controls flow rates of an oxygen gas to a user, data, for an elapsed time, of at least one of a blood oxygen level of the user and a carbon dioxide partial pressure in arterial blood (PaCO2) level of the user,
an arithmetic logical unit that calculates, from the data, proportions of durations, respective to ones of the flow rates, during which the at least one of the blood oxygen level of the user and the PaCO2 level of the user is in a prescribed range, and
a display unit that displays the proportions of the durations calculated by the arithmetic logical unit, and
wherein the oxygen inhalation therapy system controls the oxygen supply device to supply the oxygen gas to the user based on the flow rates and the proportions.

2. The oxygen inhalation therapy system according to claim 1, wherein the blood oxygen level is percutaneous arterial oxygen saturation (SpO2) measured using a pulse oximeter.

3. The oxygen inhalation therapy system according to claim 1, wherein the oxygen supply device is an oxygen concentration device.

4. The oxygen inhalation therapy system according to claim 1, wherein the oxygen supply device supplies a high-pressure oxygen gas filled in cylinder as the oxygen gas.

5. The oxygen inhalation therapy system according to claim 1, wherein the proportions of the durations are displayed as at least one of a histogram and a pie graph on the display unit.

6. The oxygen inhalation therapy system according to claim 1, wherein the proportions of the durations are displayed as at least one of a histogram and a pie graph on the display unit for at least one selected from a flow rate value of the oxygen gas, the blood oxygen level of the user, and the PaCO2 level of the user.

7. The oxygen inhalation therapy system according to claim 1,
wherein the oxygen supply device controls the flow rates of the oxygen gas based on the prescribed range and at least one of the blood oxygen level and the PaCO2 level of the user.

8. The oxygen inhalation therapy system according to claim 1,
wherein the arithmetic logical unit further, from the data and of the proportions and durations, calculates:
a first proportion of a first duration in which the blood oxygen level of the user and the PaCO2 level of the user are in the prescribed range, and
a second proportion of a second duration in which the blood oxygen level of the user and the PaCO2 level of the user are in the prescribed range, and
wherein the display unit displays the first proportion and the second proportion as at least one of a histogram and a pie graph alongside values of the blood oxygen level of the user and the PaCO2 level of the user during each of the first duration and the second duration.

9. The oxygen inhalation therapy system according to claim 1,
wherein the display unit comprises a display to a healthcare worker and is separated from and connected to, by a telecommunication network, the oxygen supply device.

10. The oxygen inhalation therapy system according to claim 1,
wherein the proportions of the durations, respective to the ones of the flow rates, are each indicative of less than entireties of the durations.

* * * * *